(12) United States Patent
D'Urso (10) Patent No.: US 11,219,441 B2
(45) Date of Patent: Jan. 11, 2022

(54) SURGICAL ACCESS RETRACTOR (71) Applicant: Paul S. D'Urso, Richmond (AU)

(72) Inventor: Paul S. D'Urso, Richmond (AU)

(73) Assignee: Paul S. D'Urso, Richmond (AU)

( * ) Notice: Subject to any disclaimer, the term of this patent is extended or adjusted under 35 U.S.C. 154(b) by 120 days.

(21) Appl. No.: 16/857,442

(22) Filed: Apr. 24, 2020

(65) Prior Publication Data

US 2020/0323522 A1 Oct. 15, 2020

Related U.S. Application Data

(63) Continuation of application No. 15/501,280, filed as application No. PCT/AU2015/050258 on May 20, 2015, now abandoned.

(30) Foreign Application Priority Data

Aug. 5, 2014 (AU) ................................ 2014100879
Aug. 5, 2014 (AU) ................................ 2014100880
Aug. 5, 2014 (AU) ................................ 2014903035

(51) Int. Cl.
*A61B 17/34* (2006.01)
*A61B 17/02* (2006.01)
(Continued)

(52) U.S. Cl.
CPC .............. *A61B 17/025* (2013.01); *A61B 5/24* (2021.01); *A61B 17/02* (2013.01); *A61B 17/0218* (2013.01); *A61B 17/3421* (2013.01); *A61B 17/3423* (2013.01); *A61B 34/10* (2016.02); *A61B 34/20* (2016.02); *A61B 90/39* (2016.02); *A61B 2017/00022* (2013.01); *A61B 2017/00526* (2013.01); *A61B 2017/00889* (2013.01); *A61B 2017/00893* (2013.01); *A61B 2017/0256* (2013.01); *A61B 2017/3445* (2013.01); *A61B 2017/568* (2013.01); *A61B 2018/00595* (2013.01); *A61B 2034/105* (2016.02);
(Continued)

(58) Field of Classification Search
CPC ........ A61B 17/3423; A61B 2017/3445; A61B 2017/568
See application file for complete search history.

(56) References Cited

U.S. PATENT DOCUMENTS

| 4,545,374 A | 10/1985 | Jacobson |
| 6,863,674 B2 | 3/2005 | Kasahara et al. |

(Continued)

FOREIGN PATENT DOCUMENTS

| CN | 103476354 A | 12/2013 |
| WO | 200001316 A1 | 1/2000 |

(Continued)

OTHER PUBLICATIONS

International Search Report issued on the PCT Application No. PCT/AU2015/050258, dated Jun. 29, 2015.
(Continued)

*Primary Examiner* — Kevin T Truong
*Assistant Examiner* — Tracy L Kamikawa
(74) *Attorney, Agent, or Firm* — Polsinelli PC (57) ABSTRACT

There is provided a patient specific access retractor for use in surgery, for example, minimally invasive spinal surgery. There are also provided methods of using the access retractor in surgery.

11 Claims, 5 Drawing Sheets

(51) Int. Cl.
*A61B 90/00* (2016.01)
*A61B 5/24* (2021.01)
*A61B 34/10* (2016.01)
*A61B 34/20* (2016.01)
*A61B 17/00* (2006.01)
*A61B 18/00* (2006.01)
*A61B 17/56* (2006.01)

(52) U.S. Cl.
CPC ............. *A61B 2034/2065* (2016.02); *A61B 2090/3966* (2016.02); *A61B 2217/005* (2013.01); *A61B 2217/007* (2013.01)

(56) References Cited

U.S. PATENT DOCUMENTS

| | | | |
|---|---|---|---|
| 8,043,212 B1 | 10/2011 | Bae et al. | |
| 8,328,815 B2 * | 12/2012 | Farr | A61B 17/025 606/99 |
| 8,425,602 B2 | 4/2013 | Guyer et al. | |
| 8,491,471 B2 * | 7/2013 | Deshmukh | A61B 17/0218 600/206 |
| 2003/0083688 A1 | 5/2003 | Simonson | |
| 2007/0208229 A1 * | 9/2007 | Prusmack | A61B 17/025 600/234 |
| 2008/0114370 A1 | 5/2008 | Schoenefeld | |
| 2008/0171930 A1 | 7/2008 | Abolfathi et al. | |
| 2009/0069635 A1 | 3/2009 | Gephart et al. | |
| 2011/0196208 A1 * | 8/2011 | Warren | A61B 1/32 600/210 |
| 2011/0237898 A1 * | 9/2011 | Stone | A61M 29/00 600/205 |
| 2011/0319745 A1 | 12/2011 | Frey | |
| 2012/0095297 A1 * | 4/2012 | Dang | A61B 17/3439 600/208 |
| 2012/0234329 A1 | 9/2012 | Vancraen et al. | |
| 2012/0271120 A1 * | 10/2012 | Seex | A61B 17/02 600/235 |
| 2013/0053854 A1 | 2/2013 | Schoenefeld et al. | |
| 2013/0218163 A1 * | 8/2013 | Frey | A61B 34/10 606/87 |
| 2013/0274778 A1 | 10/2013 | Mercier et al. | |
| 2013/0317303 A1 | 11/2013 | Deshmukh et al. | |
| 2014/0350614 A1 * | 11/2014 | Frey | A61F 2/4611 606/86 R |

FOREIGN PATENT DOCUMENTS

| | | |
|---|---|---|
| WO | 20110299934 A1 | 3/2011 |
| WO | 2012024281 A2 | 2/2012 |
| WO | 2013158521 A1 | 10/2013 |

OTHER PUBLICATIONS

Supplementary European Search Report dated Jun. 14, 2018 in European Application No. EP 15829770.
Supplementary European Search Report dated Mar. 2, 2018 in European Application No. EP 15830479.

* cited by examiner

SURGICAL ACCESS RETRACTOR

CROSS-REFERENCE TO RELATED APPLICATIONS

This application claims priority to and is a continuation of U.S. patent application Ser. No. 15/501,280, filed on Feb. 2, 2017, which claims the benefit and is a 371 of international PCT/AU2015/050258, filed on May 20, 2015, which claims priority of Australian Application No. 2014100879, filed on Aug. 5, 2014, Australian Application No. 2014100880, filed on Aug. 5, 2014, and Australian Application No. 2014903035, filed on Aug. 5, 2014, the entirety of which is herein incorporated by reference.

FIELD

The present disclosure relates generally to a surgical access retractor. More specifically, the disclosure is directed to a minimally invasive surgical access retractor and a method of minimally invasive retraction that expands the field of operation.

BACKGROUND

In recent years, minimally invasive surgical (MIS) approaches have been applied to orthopaedic surgery and more recently to spine surgery, such as instrumented fusions involving one or more vertebral bodies.

The evolution of MIS surgery has been dependent on the development of new technologies. Such technologies include prosthetic devices such as screws and rods and interbody fusion cages and access retractors, to allow the surgeon to perform placement of such devices via small incisions and openings in the patient's body.

In regard to the lumbar spine, minimally invasive surgical technique may be applied to the operation of transforaminal lumbar interbody fusion (TLIF). A minimally invasive transforaminal lumbar interbody fusion may be performed by four small 2 cm incisions in the lumbar region. The incisions are used to place pedicle screws and one of the incisions is used to place a retractor system so that the surgeon can see the anatomical elements such as the nerve roots and the intervertebral disc. The surgeon uses a retractor to perform laminectomy to decompress the associated exiting nerve roots, perform lumbar discectomy and prepare the interbody space and then place bone graft and an interbody cage to facilitate interbody fusion. The MIS TLIF has evolved to a stage where a surgery can be performed in a highly repeatable fashion with a high degree of safety and reliability of outcome.

Minimally invasive surgical procedures may involve the use of a series of muscle dilators that separate the muscle fibers of the spine to create a pathway to the spine. A Kirschner wire (K-wire) is initially introduced through a small incision and directed towards the spinal pathology. The position of the K-wire may be visualized by a fluoroscopic imaging system to identify its location. An initial narrow diameter muscle dilator is passed over the K-wire, and the K-wire is removed and subsequent larger muscle dilators are continually passed. When the opening is large enough, an access tube or retractor is positioned around the last muscle dilator through which the surgery is performed. The inner sequential muscle dilators are then removed allowing the surgeon to operate through the tubular retractor.

Furthermore a surgical device company will commonly provide a retractor set for surgery, and such a retractor set often requires multiple retractors of varying diameters and lengths as well as attachment ends to the operating table. As standard surgery requires many instruments and devices to perform the surgery, it incurs a substantial logistic cost. This involves:

cleaning, sterilisation and processing of all components prior to each procedure;
delivery and transfer of components from the device company warehouse to and from the hospital is time consuming and expensive;
such stock must be replaced and accounted for and can be difficult to track and validate.

Therefore, a continuing need exists for an improved device, an improved system, and an improved method for performing surgery, particularly minimally invasive spinal surgery.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

SUMMARY

In one aspect there is provided a surgical access retractor for maintaining an enlarged surgical corridor, said retractor having a length sufficient to span from a skin surface through to a region of surgical interest, said retractor having at least a portion thereof shaped to match with the region of surgical interest, wherein the shaped portion is, at least partly, based on patient specific medical imaging.

The region of surgical interest may be a vertebral body. The region of surgical interest may be a pedicle.

The access retractor may be patient specific through matching the shaped portion to the morphology of the region of surgical interest. As the retractor may dock on patient anatomy in a specific way, fixation of the retractor to the anatomy may be facilitated. Fixation of the retractor to the patient anatomy may provide surgical access in an accurate, reliable and safe fashion. The specific retractor may be used as a guide to perform, for example, osteotomy and in the placement of, for example, intervertebral prosthesis and bone graft.

Advantageously, the patient specific access retractor obviates the need to have retractors of various sizes available at the time of surgery. This substantially reduces the logistics and cost of preparation of instruments for surgery.

The access retractor may be patient specific and procedure specific.

The shaped portion of the retractor may comprise one or more apertures or fixation means for securing the retractor to the region of surgical interest.

The retractor may comprise a lip on the top face which, in use, is placed externally on a patient's skin.

The angle of the lip may be customised based on patient specific medical imaging.

The lip may comprise at least one aperture or fixation means for securing the retractor to a patient's skin.

Fixation of the retractor both at the region of surgical interest and at the patient's skin is advantageous as it obviates the need for extraneous attachment, such as via an arm to a surgical table.

As the retractor is patient specific, various features may be included in the retractor design which are also patient specific. The placement of features in the retractor may be enabled through patient imaging and computer aided design. The features may be, at least partly, located in the shaped portion of the access retractor.

Specific grooves or channels may be incorporated into the retractor to conform with the contour of the retractor and/or conform with patient specific anatomy, in such a way as to mark, localise or perform predetermined surgical intervention. In this way, the access retractor may be used to guide instruments; for example to perform osteotomy, monitor neural function, guide instruments to perform intervertebral disc clearance and preparation or to guide, place and deliver an intervertebral cage prosthesis in an accurate manner.

The shaped portion may comprise one or more guides for cutting bone. The guides may be positioned in the retractor based on preoperative medical imaging.

These features are selected and predesigned into the retractor so that the surgeon may accurately perform procedures.

The retractor may be designed by using a combination of computer aided design software and patient morphological data obtained by medical imaging. For example, vectors may be determined to run along the centre of pedicles of the spine. In this way the intersection of the vector with the surface of the patient's skin may be precisely determined. Further, the length of the vector from the surface of the skin to the intersection with a particular region of surgical interest, such as a bone interface, may be determined.

Through the characterisation of the vector, computer design software may be used to create patient specific dilators to allow progressive dilation of a patient's tissue to a predetermined depth and circumference around the vector replicated by, for example, a wire, such that the patient specific access retractor can be implanted into the patient.

The patient specific access retractor may incorporate a predesignated vector so that it may be guided by way of a K-wire to allow precise placement of the access retractor onto the anatomy to be localized, such as the spine. The point of contact of the retractor with both the skin surface, and the anatomy to be localised at the base of the retractor may be contoured in a patient specific manner using computer aided design software.

Once the patient specific shape of the retractor is determined, the retractor may be manufactured using three-dimensional printing.

One or more fixation points corresponding to the intersection of the vector with the selected anatomy may be incorporated into the retractor. The fixation may be by way of a cannulated screw which is guided down a K-wire and inserted into the patient's bone in such a way that the retractor is then secured to the bone. It will be appreciated that a cannulated screw is one method of securing the retractor. Other methods may include staples or pins.

The patient specific retractor may also incorporate ancillary channels to allow suction of fluid from the internal aperture of the device or irrigation of fluid into the internal aperture of the device.

Dilators may be used to assist in placement of the access retractor and may incorporate components that allow electrocautery by way of diathermy to be used at the tip of the dilator where the interface of tissue and bone occurs. Such dilators may also include components that allow neurophysiological monitoring of the surrounding tissue and associated structures. The dilators may also contain channels to allow irrigation and suction to occur.

The patient specific retractor may also incorporate components to allow diathermy and cauterisation of surrounding tissue.

The patient specific retractor may be impregnated with antimicrobial substances or surface coatings to reduce the risk of infection.

The patient specific retractor may incorporate radio-opaque markers to allow verification of positioning by way of image intensification. Preferably this would not be to the extent that they would obscure patient anatomy.

The patient specific retractor may facilitate localisation to other areas of anatomy, for example to harvest bone graft without instruments or for reconstructing donor site anatomy.

The access retractor may also incorporate components to allow electrophysiological monitoring of surrounding structures and tissue.

Furthermore a guide or groove within the retractor may be used to facilitate suction or aspiration of fluid and gas from the working area.

Furthermore an access aperture or groove may be used to facilitate irrigation of fluid into the working area.

Electrophysiological sensors may be placed beside the access retractor in pre-set locations to facilitate neural monitoring in the working area.

The retractor may comprise any combination of the hereinbefore disclosed embodiments.

In another aspect there is provided a method for designing a patient specific access retractor comprising the steps of:
a) determining one or more trajectories from a region of surgical interest to the skin surface of a patient using preoperative medical imaging;
b) determining the morphology of the region of surgical interest using preoperative medical imaging; and
c) designing an access retractor, said retractor having a length sufficient to span from a skin surface through to the region of surgical interest, said retractor having at least one portion shaped to dock with the region of surgical interest, wherein the shape of said portion is based, at least in part, on patient specific medical imaging.

In another aspect there is provided a method for manufacturing a patient specific access retractor comprising the steps of:
a) determining one or more trajectories from a region of surgical interest to the skin surface of a patient using preoperative medical imaging;
b) determining the morphology of the region of surgical interest using preoperative medical imaging;
c) designing an access retractor, said retractor having a length sufficient to span from a skin surface through to the region of surgical interest, said retractor having at least one portion shaped to dock with the region of surgical interest, wherein the shape of said portion is based, at least in part, on patient specific medical imaging; and
d) manufacturing the access retractor.

In any of the hereinbefore disclosed embodiments the region of surgical interest may be an anatomical body.

In any of the hereinbefore disclosed embodiments the anatomical body may be a vertebral body. The vertebral body may be a pedicle.

In any of the hereinbefore disclose embodiments the medical imaging may be computed tomography.

In any of the hereinbefore disclosed embodiments the access retractor may be manufactured using rapid prototype technology.

In any of the hereinbefore disclosed embodiments the access retractor may be manufactured using three-dimensional printing.

In any of the hereinbefore disclosed embodiments the trajectories may be represented as three-dimensional images with the aid of suitable computer software. The trajectories may be determined to meet the skin at particular entry points.

The access retractor may be manufactured from a suitable compatible polymer, such as, for example, polyether ether ketone.

In another aspect there is provided a use of an access retractor as hereinbefore disclosed in a surgical procedure. The surgical procedure may be spinal surgery. The surgical procedure may be minimally invasive spinal surgery. The surgical procedure may be spinal fusion. The surgical procedure may be transforaminal lumbar interbody fusion (TLIF).

In another aspect there is provided a method for accessing a region of surgical interested comprising the steps of:
 a) providing a retractor according to any one of the hereinbefore disclosed embodiments;
 b) docking at least part of the shaped portion of the retractor via a surgical corridor to the region of surgical interest; and
 c) fixing said retractor to the region of surgical interest.

The retractor may also be fixed to the skin of the patient via a suitable fixation method. For example via an aperture in the lip of the retractor.

Throughout this specification, use of the terms "comprises" or "comprising" or grammatical variations thereon shall be taken to specify the presence of stated features, integers, steps or components but does not preclude the presence or addition of one or more other features, integers, steps, components or groups thereof not specifically mentioned.

DESCRIPTION OF EXEMPLARY EMBODIMENTS

Before the present devices and/or methods are disclosed and described, it is to be understood that unless otherwise indicated this disclosure is not limited to specific devices, components, designs, methods, or the like, as such may vary, unless otherwise specified. It is also to be understood that the terminology used herein is for the purpose of describing particular embodiments only and is not intended to be limiting.

It must also be noted that, as used in the specification and the appended claims, the singular forms 'a', 'an' and 'the' include plural referents unless otherwise specified. Thus, for example, reference to 'a guide wire' may include more than one guide wires, and the like.

Disclosed herein are advantageous devices and methods for performing surgery, particularly spinal fusion surgery.

In an exemplary embodiment a patient specific access retractor is provided. Once the depth of tissue to be accessed by the retractor is known from patient medical imaging, standard design may be applied to the external or top part of the retractor. This may extend to approximately 80% of the depth of the access retractor. The final approximately 20% may be designed in a specific way to contour match the morphology of the patient's anatomy and in particular, the region of surgical interest.

A guidance aperture may be within the retractor where a Nitinol K-wire is used to localise the retractor to the patient specific anatomy. The guidance aperture may also allow placement of a cannulated screw to secure the retractor to the patient's spine. Within the guidance aperture may be specially designed grooves, which facilitate placement of instruments in locations within the working area of the access retractor. Such grooves may be used to place mark-to-mark osteotomy lines on the patient's bone and then guide instruments into the interbody space. The access retractor may also comprise an attachment for a Nitinol K-wire on the rosteral side of the intervertebral disc to be operated on. This facilitates attachment of the access retractor to the patient. The access retractor may have apertures or instrument guides such that a fibre optic light source may be attached. The access retractor may have a guide or facility for the use of diathermy at the base of the retractor. The customised portion of the retractor may have diathermy points or a guide for the use of such points in the equipment such that the tissue can be cauterised.

In order to evolve the manufacturing procedure to a greater level of ergonomic efficiency, safety and best possible patient outcomes, three-dimensional printing technology has been used to facilitate these outcomes.

Three-dimensional printing is a process whereby layer based polymerisation of a resin or powder is used to produce a solid object. This technology has been applied to producing solid replicas of anatomy which has been captured by medical imaging.

Three-dimensional printing technology has been used extensively in computerised design product development prototyping and more recently direct manufacturing of objects. It has been possible to integrate computer design and anatomical biomodeling information to provide customised prosthetic implants for the human body. This disclosure uses rapid prototyping technology to facilitate interbody fusion by way of the minimally invasive transforaminal interbody fusion technique. Three-dimensional bench top printing has been integrated with diagnostic surgical planning, surgical navigation and by way of patient specific minimally invasive access retractors.

The patient specific access retractor may also be used for harvesting bone graft. A second retractor may be manufactured by three-dimensional printing to dock on the iliac crest or other part of the skeleton to harvest bone graft. In this embodiment, a vector is created from either the right or left iliac crest which crosses the skin at the same point, if possible, as one of the vectors identifying the pedicle of the selected vertebra. Alternatively, a vector exiting at a separate point would be another option. The depth of tissue from the surface to the iliac crest or bone donor site is determined. The retractor is again contour matched to the surface of the iliac crest or bone donor site and the length and diameter of the retractor is then constructed in three-dimensional design software. The retractor incorporates a guide for placement along a K-wire that has been fixed to the iliac crest bone donor site. The retractor is then manufactured by way of three-dimensional printing in a bio-compatible material. At the time of surgery, the surgeon places a Jamshidi needle into the iliac crest or suitable bone donor site and places a K-wire. The K-wire is then used to guide the retractor to the iliac crest or bone donor site and a cannulated screw is then used to secure the retractor to the crest. The retractor may act to guide instruments to harvest bone graft by way of specific channels and grooves within the retractor.

Figure 1A:
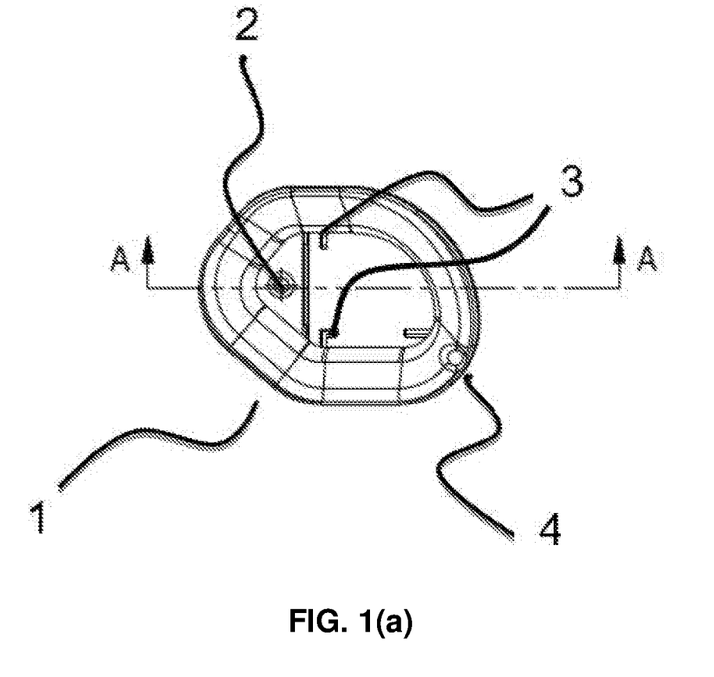
FIG. 1(a) is a plan view of an access retractor according to an embodiment of the present disclosure.
Figure 1B:
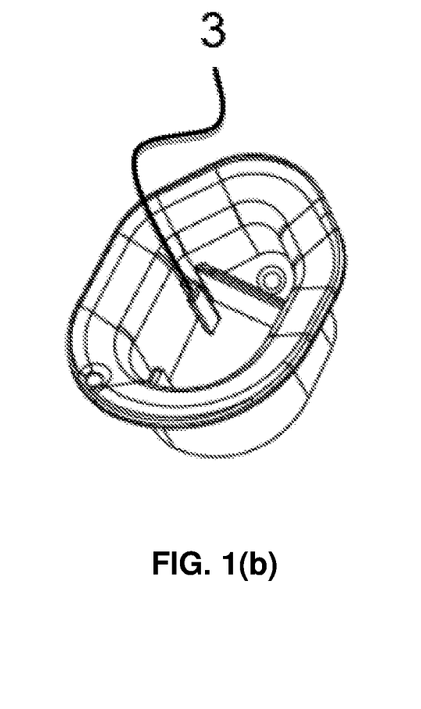
FIG. 1(b) is a plan view of an access retractor according to an embodiment of the present disclosure.
Figure 1C:
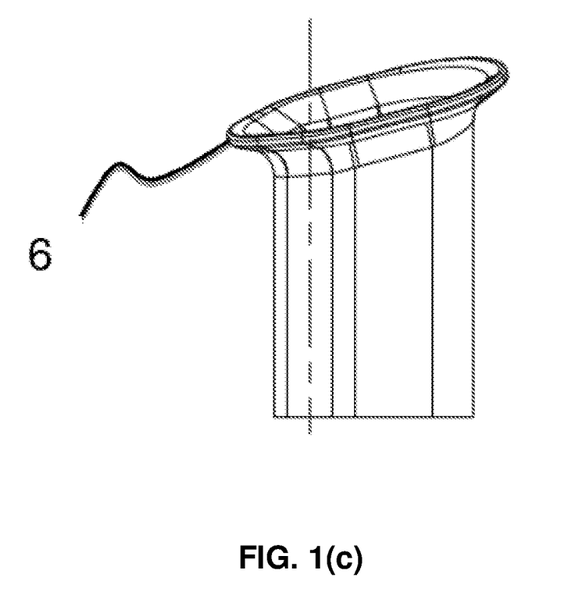
FIG. 1(c) is a side elevation of an access retractor according to an embodiment of the present disclosure.

Referring to FIG. 1(a), access retractor (1) is illustrated. The retractor has a fixation point (2), located on the shaped portion of the retractor, for fixing to an anatomical body and guides (3) to facilitate, for example, the introduction of instruments. An aperture (4) on the retractor lip is available to secure the retractor to the patient's skin. Referring to FIG. 1(b), a guide (3) for instrument introduction is highlighted. Referring to FIG. 1(c), lip (6) is angled based on patient specific medical imaging.

Figure 1D:
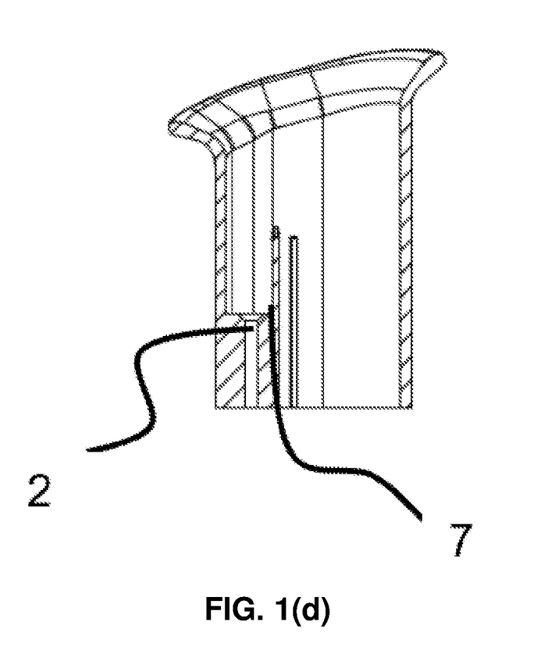
FIG. 1(d) shows a section through plane A-A of the access retractor of FIG. 1(a) according to an embodiment of the present disclosure.

FIG. 1(d) depicts a section A-A through retractor (1) of FIG. 1(a). The section shows fixation point (2) and other shaped structure (7).

Figure 1E:
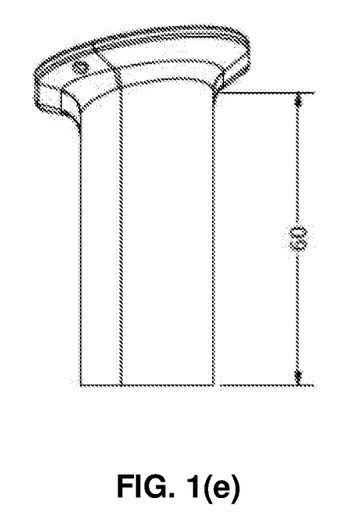
FIG. 1(e) shows a side elevation of an access retractor according to an embodiment of the present disclosure.

FIG. 1(e) indicates the length of the retractor to be 60 mm, that is, the length from the region of surgical interest to the surface of the skin.

While the foregoing description has focused on spinal surgery, it is contemplated that the retractors and methods described herein may find use in a wide range of surgical applications. Thus, where it is desired to insert a screw or pin into bone in a minimally invasive manner, or otherwise to access a surgical target site via an instrument, the retractors and dilators of the present disclosure may be used.

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the above examples are put forth so as to provide those skilled in the art with a complete disclosure and description of how to make and use the disclosed devices, and are not intended to limit the scope of the disclosure.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

All documents cited are herein fully incorporated by reference for all jurisdictions in which such incorporation is permitted and to the extent such disclosure is consistent with the description of the present disclosure.

What is claimed is:

1. A method of using a surgical access retractor in spinal surgery comprising:
    (a) providing a surgical access retractor, said access retractor having a length sufficient to span from a skin surface through to a pedicle; said access retractor having at least one portion shaped to match with the pedicle, wherein the shape of said portion is, at least in part, based on patient specific medical imaging; wherein said shaped portion comprises one or more enclosed apertures for securing the retractor to the pedicle; and wherein said access retractor comprises a lip on a top face, wherein said lip comprises at least one enclosed aperture for securing the retractor to a patient's skin;
    (b) localizing the pedicle via a surgical corridor by way of a K-wire;
    (c) inserting the K-wire through one of the enclosed apertures on the shaped portion of said access retractor;
    (d) guiding said access retractor by way of the K-wire to dock the shaped portion to the pedicle via the surgical corridor;
    (e) guiding a cannulated screw down the K-wire and through the one of the enclosed apertures on the shaped portion;
    (f) securing said access retractor to the pedicle by means of the cannulated screw; and
    (g) securing said access retractor to the patient's skin by means of the at least one aperture on the lip.

2. The method according to claim 1, wherein the length sufficient to span from the skin surface through to the pedicle is determined by the patient specific medical imaging.

3. The method according to claim 1, wherein an angle of the lip is customised based on the patient specific medical imaging.

4. A method according to claim 1, wherein the shaped portion comprises one or more guides for the introduction of instruments.

5. The method according to claim 1, wherein the shaped portion comprises specific grooves or channels to mark, localise or perform predetermined surgical intervention.

6. The method according to claim 1, wherein the retractor comprises components to allow diathermy and cauterisation of surrounding tissue.

7. The method according to claim 1, wherein the retractor comprises antimicrobial substances or surface coatings to reduce the risk of infection.

8. The method according to claim 1, wherein the retractor comprises radio-opaque markers to allow verification of positioning by way of image intensification.

9. The method according to claim 1, wherein, in use, electrophysiological sensors are placed beside the access retractor in preset locations to facilitate neural monitoring in a working area of the access retractor.

10. The method according to claim 1, wherein the retractor comprises ancillary channels to allow suction of fluid from an internal aperture of the retractor or irrigation of fluid into the internal aperture of the retractor.

11. The method according to claim 1, wherein prior to docking the shaped portion of the retractor to the pedicle one or more dilators are utilized to increase a width of the surgical corridor.

* * * * *